(12) United States Patent
Kassem et al.

(10) Patent No.: US 9,050,001 B2
(45) Date of Patent: Jun. 9, 2015

(54) READING DEVICE IN WIRED COMMUNICATION WITH A PROBE HAVING AN EMBEDDED MEMORY DEVICE

(75) Inventors: Salim Kassem, North Attleboro, MA (US); Didier Balli, La Chaux-de-Fonds (CH); Nicholas D. Baruch, N. Smithfield, RI (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 480 days.

(21) Appl. No.: 13/434,723

(22) Filed: Mar. 29, 2012

(65) Prior Publication Data

US 2013/0257465 A1    Oct. 3, 2013

(51) Int. Cl.
*G01R 27/08* (2006.01)
*A61B 5/03* (2006.01)
*G01L 9/04* (2006.01)

(52) U.S. Cl.
CPC . *A61B 5/031* (2013.01); *A61B 5/03* (2013.01); *A61B 2560/0271* (2013.01); *A61B 2562/08* (2013.01); *A61B 2562/166* (2013.01); *A61B 2562/222* (2013.01); *G01L 9/04* (2013.01)

(58) Field of Classification Search
CPC ............................ A61B 5/0205; A61B 5/6833
USPC ............................. 324/706; 600/513; 607/59
See application file for complete search history.

(56) References Cited

U.S. PATENT DOCUMENTS

| | | |
|---|---|---|
| 4,315,210 A | 2/1982 | Michel et al. |
| 4,366,714 A * | 1/1983 | Adorni ............................ 73/708 |
| 4,580,557 A | 4/1986 | Hertzmann |
| 4,621,643 A | 11/1986 | New, Jr. et al. |
| 4,722,337 A | 2/1988 | Losch et al. |
| 4,858,615 A | 8/1989 | Meinema |
| 4,897,789 A | 1/1990 | King et al. |
| 4,958,520 A | 9/1990 | Trommler et al. |
| 5,133,219 A | 7/1992 | Camp |
| 5,383,874 A | 1/1995 | Jackson et al. |
| 5,540,683 A | 7/1996 | Ichikawa et al. |
| 5,660,567 A | 8/1997 | Nierlich et al. |
| 5,711,302 A | 1/1998 | Lampropoulos et al. |
| 6,106,498 A | 8/2000 | Friedli et al. |
| 6,190,326 B1 | 2/2001 | McKinnon et al. |
| 6,204,668 B1 | 3/2001 | Sequeira et al. |
| 6,377,829 B1 | 4/2002 | Al-Ali |
| 6,468,241 B1 | 10/2002 | Gelfand et al. |
| 6,651,669 B1 | 11/2003 | Burnside |
| 6,652,514 B2 | 11/2003 | Ellman et al. |
| 6,676,600 B1 | 1/2004 | Conero et al. |
| 6,695,806 B2 | 2/2004 | Gelfand et al. |
| 6,725,075 B2 | 4/2004 | Al-Ali |
| 7,213,439 B2 | 5/2007 | Trainoff |
| 7,248,910 B2 | 7/2007 | Li et al. |

(Continued)

*Primary Examiner* — Benjamin M Baldridge
(74) *Attorney, Agent, or Firm* — Cohen & Hildebrand, PLLC

(57) ABSTRACT

A monitoring system including a reading device electrically connected to a probe via a wired interface. The probe has a physiological sensor/transducer configured as a Wheatstone resistive bridge balancing circuit. Integrated within the housing of the probe to prohibit separation during use by a user is a memory device arranged in parallel with the sensor. Communication between the reading device and the probe occurs via a wired interface utilizing a same number of electrical wires between the reading device and the Wheatstone as would be required without the memory device. Control circuitry selects between one of two modes for accessing either data detected by the sensor or the memory device.

19 Claims, 4 Drawing Sheets

(56) References Cited

U.S. PATENT DOCUMENTS

| | | | |
|---|---|---|---|
| 8,671,237 B2* | 3/2014 | Ma et al. | 710/313 |
| 2002/0026455 A1* | 2/2002 | Toothman et al. | 707/204 |
| 2004/0006263 A1* | 1/2004 | Anderson et al. | 600/364 |
| 2005/0049501 A1 | 3/2005 | Conero et al. | |
| 2005/0101843 A1 | 5/2005 | Quinn et al. | |
| 2005/0113704 A1* | 5/2005 | Lawson et al. | 600/513 |
| 2006/0036137 A1* | 2/2006 | Lewicke | 600/301 |
| 2009/0112147 A1 | 4/2009 | Kassem | |
| 2009/0112308 A1 | 4/2009 | Kassem | |
| 2009/0165564 A1 | 7/2009 | Matsushima et al. | |
| 2009/0192572 A1* | 7/2009 | Dal Molin et al. | 607/59 |
| 2010/0241787 A1* | 9/2010 | Goldman et al. | 711/103 |
| 2010/0274099 A1* | 10/2010 | Telfort et al. | 600/300 |
| 2011/0034789 A1* | 2/2011 | Haisley | 600/324 |
| 2011/0118563 A1* | 5/2011 | Lee et al. | 600/301 |

* cited by examiner

US 9,050,001 B2

READING DEVICE IN WIRED COMMUNICATION WITH A PROBE HAVING AN EMBEDDED MEMORY DEVICE

BACKGROUND OF THE INVENTION

1. Field of the Invention

The present invention is directed to a monitoring system and method for operating the system including a reading device in wired communication with a probe. In particular, the present invention is directed to a monitoring system in which the reading device is in wired communication with a probe having a memory device embedded therein to prohibit being separated from a sensor by the user during use.

2. Description of Related Art

Medical probes comprising one or more physiological sensors or transducers are used to measure parameters such as, but not limited to, pressure, tension or displacement. Such probes may be external to the body or implantable within the body. Some sensors or transducers such as pressure sensors are typically designed as a resistive bridge balancing circuit (e.g., a Wheatstone bridge). When using a sensor or transducer a non-volatile read/write memory may be required to store data such as calibration parameters (e.g., zeroing, temperature coefficient), information associated with a patient (e.g., age) and/or equipment information (e.g., probe expiration date, probe usage time and/or failure mode information (for instance, recovery data in case of memory corruption)). As an illustrative example, the medical probe may be a differential pressure sensor for measuring intracranial pressure (ICP) within the brain. In such application, prior to implantation of a device (e.g., implantable ICP solid state sensor) an ambient pressure reference value, also referred to as "zero reference value" or "offset reference value," is detected and stored in a memory. Typically, the zero or offset pressure reference value is measured when the sensor is wet by soaking the tip in a shallow pool of sterile water or sterile saline for a predetermined period of time (e.g., approximately 15 minutes to approximately 30 minutes). Alternatively, the zero or offset reference value (e.g., offset pressure value) may be measured in air. During use, each measurement value detected by the sensor is compensated or offset by the previously calibrated offset reference value to produce a compensated value.

Reading of information from or writing of information to the memory device associated with the probe by a separate reading device occurs via a communication interface (e.g., wireless or wired). A wireless communication interface using such technology as bar code scanning is limited to reading information stored in the memory associated with the probe. Writing or storing of new information to the memory device is not permitted with bar code scanning. Other commonly used wireless technology such as Radio Frequency Identification (RFID) disadvantageously increases the overall complexity due to the additional circuitry and components required.

Alternatively, a wired connection via an interface cable may be used to transmit information to and from the reading device, wherein the probe and a memory device are embedded within the interface cable itself. The zero or offset reference value stored in memory must undesirably be reentered/acknowledged whenever interface cables used to connect the probe to the reading device are replaced or even when the same interface cables are used to reconnect the probe to the reading device. Furthermore, a reusable interface cable that requires sterilization, (e.g., autoclaved), may possibly result in physical damage to the memory. Thus, embedding of the memory device in the interface cables disadvantageously permits the memory device to be separated from the probe itself. For either a reusable or one-time-usage probe capable of being powered off or disconnected while in use, it is preferable that separation of the memory from the probe by the patient while in use be prohibited in order to: (i) avoid the possibility of crossing the probe with a memory associated with a different probe and thus avoid the use of wrong data; (ii) retain data stored within the memory device even in the absence of power; and (iii) reduce complexity of confirming the zero value associated with a probe.

It is therefore desirable to develop a probe with a memory device embedded therein that prohibits separation by the user during use while simultaneously minimizing the overall footprint of the probe and the number of wires/lines/electrical connections between the probe and a separate reading device.

SUMMARY OF THE INVENTION

The present invention is directed to a probe with a memory device embedded therein that prohibits separation by the user during use while simultaneously minimizing the overall footprint of the probe and the number of wires/lines/electrical connections between the probe and a separate reading device.

One aspect of the present invention is directed to a monitoring system including a reading device electrically connected to a probe via a wired interface. The probe has a physiological sensor/transducer configured as a Wheatstone resistive bridge balancing circuit. Integrated within the housing of the probe to prohibit separation during use by a user is a memory device arranged in parallel with the sensor. Communication between the reading device and the probe occurs via a wired interface utilizing a same number of electrical connections between the reading device and the Wheatstone resistive bridge balancing circuit as would be required if the memory device was eliminated. Control circuitry controls selection between one of two modes for accessing either sensor signal response or data from the memory device.

Another aspect of the present invention relates to a method for operating the monitoring system described in the preceding paragraph. Specifically, the method includes the step of configuring, via a control signal generated by the control circuitry, the position of each switch so as to select between the two modes.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which.

DETAILED DESCRIPTION OF THE INVENTION

The present invention discloses a monitoring system including a reading device (e.g., external bedside monitor or neuro-monitor) connected via a wired interface (e.g., one or more interface cables) to a probe. The probe includes one or more physiological sensors or transducers configured as a Wheatstone resistive bridge balancing circuit. Embedded, included or integrated within the housing of the probe is a memory device such that the sensor and memory device are prohibited from being separated from one another during use by a user. The memory device is preferably a non-volatile memory device.

Figure 1:
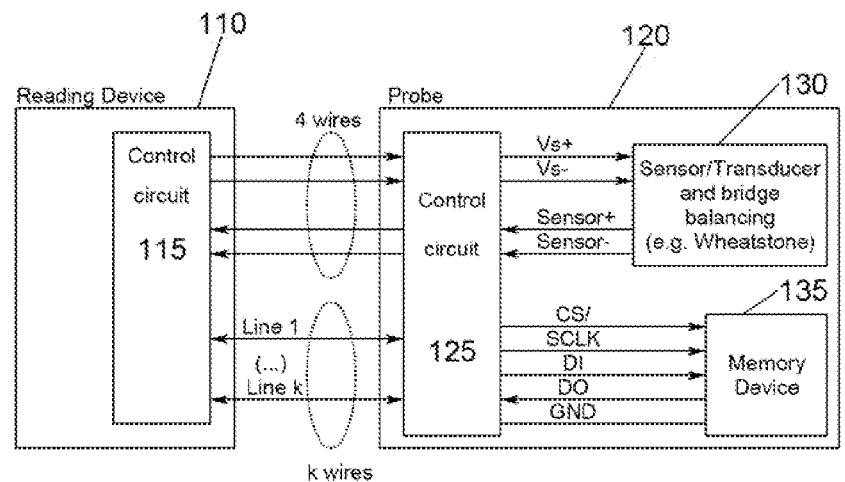
FIG. 1 is an exemplary schematic diagram of a prior art monitoring system including a reading unit communicating via several wire-lines/connections with a probe having a memory device embedded therein.

Many different types of memory devices are available of which the number of electrical wire-line connections required vary. FIG. 1, is a prior art system wherein four wires-lines plus an additional k wires-lines (where k≥1) electrically connect electronic control circuits 115, 125 associated with external reading device 110 (e.g., a neuro monitor) and probe 120, respectively. Thus, at a minimum, when k=1, five wires-lines are required between the control circuits 115, 125. Electronic control circuitry 125 in probe 120 is electrically connected in series with sensor/transducer 130 and a Serial Peripheral Interface (SPI) memory device 135. Memory device 135 is accessed by the external reading device 110 via electronic control circuitry 125. Electronic control circuits 115, 125 connect the sensor(s)/transducer(s) of probe 120 to the external reading device 110 in order to access physiological measurements and/or other data from the sensor(s)/transducer(s). Electronic control circuitry 125 employs four wires-lines plus an additional k wires-lines (where k≥1) in order to connect the sensor/transducer 130 or the memory 135 to the external reading device 110. In this prior art configuration the additional circuitry (electronic control circuitry 125) and k additional wires-lines disadvantageously increase the overall cost and size of the footprint and the interface cable section. Even in the case in which electronic control circuitry 125 is eliminated altogether by electrically connecting circuit 115 directly to the sensor 130 and memory 135, the additional wire-line electrical connections still increase the overall cost.

Alternatively, it is also well known in the art to substitute an I2C memory device for the SPI memory device in FIG. 1. Despite the number of wires-lines desirably being reduced from that of the SPI memory device, the need for additional wire-line connections required when using the I2C memory chip relative to that without the embedded memory device still increases the overall cost of manufacture and the size of the probe footprint. The overall cost of manufacture is always a concern, but with some applications, most notably, intracranial pressure, minimizing the footprint size of the probe is a significant factor in its design configuration. It is therefore desirable to utilize a design that minimizes the number of wire-line connections between the memory device embedded in the probe and the separate external reading device. In particular, for existing products, it is desirable to embed within the probe a one-wire memory device in which the number of wires-lines required is equal to that without the memory device in the probe.

Figure 2A:
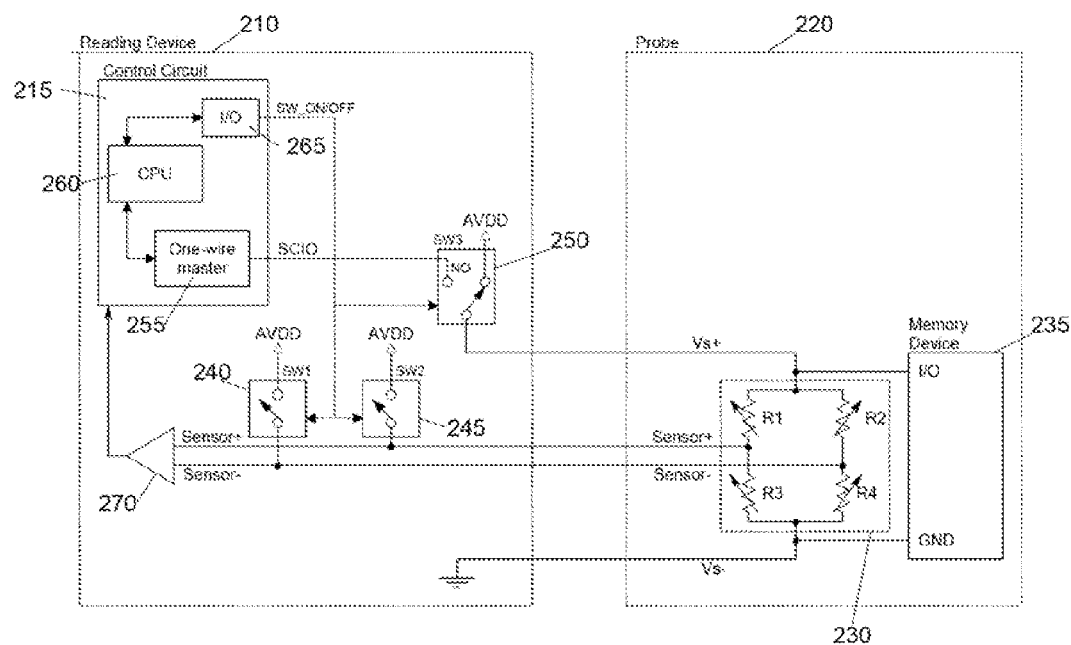
FIG. 2A is an exemplary schematic diagram of a system in accordance with the present invention including a reading device having three switches communicating via a one-wire protocol using a One-Wire® Master with a probe having a resistive Wheatstone bridge and a slave One-Wire® memory device embedded therein.

FIG. 2A is such an exemplary system in accordance with the present invention wherein the probe has embedded therein a memory device (i.e., a "one-wire memory device") (for example, a One-Wire® EEPROM memory device manufactured by Maxim Integrated Products, Inc.) requiring only two pins, contacts or electrical wires, i.e., one for ground and the other for the Data/Power supply. In addition, the circuit design or configuration in accordance with the present invention permits sharing of common wire-line connections thereby utilizing the same number of wires-lines (e.g., four wires-lines, not including the shield connection) for interfacing between reading unit 210 and either the sensor/transducers 230 or the memory device 235 as would be required without the memory device. Moreover, the need for additional circuitry (e.g., control circuitry 125 associated with the probe as shown in prior art FIG. 1) is eliminated and thus the overall size of the footprint is reduced by arranging the One-Wire® memory device 235 in parallel with the sensor/transducer 230. Electronic control circuitry 215 allows external reading device 210 to access (e.g., reading of data from/writing data to) the One-Wire® non-volatile memory device 235 embedded in the probe 220. Supply voltage and electronics around the One-Wire® memory device are designed in such way that the One-Wire® device works within manufacturer specifications (e.g., I/O logical level, I/O current sink, etc.)

In the system 200 in FIG. 2A, external reading device 210 is electrically connected to probe 220 via 4 wires-lines. Probe 220 includes an EEPROM memory device 235, preferably a One-Wire® EEPROM memory device such as DS2431 a 1024-bit, one-wire EEPROM chip manufactured by Maxim Integrated Products, Inc. Although probe 220, as depicted in FIG. 2A, has only a one-wire memory device, it is contemplated and within the intended scope of the present invention to include additional one-wire devices such as, but not limited to, a DS 18520 One-Wire® Digital Thermometer manufactured by Maxim Integrated Products, Inc., arranged in parallel with the one-wire memory device 235. The one-wire memory device may be selected to also include an additional digital port, wherein the digital signals received via the port may specifically configure the sensor, for example, during a self-test or a calibration. One such additional digital port may be provided using a DS28E04-100, 4096-bit, One-Wire® EEPROM chip manufactured by Maxim Integrated Products having two general-purpose I/O ports that can be used for input or to generate level and/or pulse outputs. Electronically connected to the One-Wire® EEPROM 235 is a sensor/transducer 230, for example, a Wheatstone resistive bridge balancing circuit (without Kelvin connections in this example) having two excitation lines (Vs+, Vs−) and two differential output voltage lines (sensor+, sensor−). As stress is applied to the strain gauge, a change in resistance unbalances the Wheatstone bridge resulting in a signal output (sensor+, sensor−), related to the stress value. Since the differential signal output value is relatively small, (typically a few hundred microvolts) a differential amplifier or instrumentation amplifier 270 is preferably employed to boost or increase the sensor output signal level to a full scale of preferably, approximately ±2.5V volts around bias voltage (e.g. using a gain of preferably approximately 128). Amplifier 270 is a separate device. It is, however, contemplated for the amplifier to be embedded within an analog-to-digital converter (ADC) such as ADS 1246 manufactured by Texas Instrument. Additional signal conditioning electronics may be employed to further process the sensor output signals.

Three switches SW1, SW2, SW3 (referred to by reference element numbers 240, 245, 250, respectively) are utilized to set or control probe 220 between one of two modes, configurations or states. Each of the switches may be analog switches, solid state relays, transistors (e.g., a P-channel MOSFET switch), photo-transistors or any combination thereof. For instance, switches SW1, SW2 may be two single pole, single throw (SPST) switches SW1, SW2 while switch SW3 is one single pole, double throw (SPDT) switch. As an alternative configuration, the one SPDT switch SW3 may be realized by using two SPST switches. A first memory access mode, configuration or state is one in which memory device 235 is accessible by the reading device 210 for reading and/or writing operations. In a second sensor access mode, configuration or state the data (e.g., physiological parameter values) detected by the sensor/transducer 230 is accessible by the reading device 210.

Electronic control circuitry 215 associated with the external reading device 210 is used to configure or control the settings of each of the switches SW1, SW2, SW3 and thus select between the two different modes. In order to access the memory device 235 to perform reading/writing operations, control circuitry 215 preferably includes a One-Wire® Master 255 manufactured by Maxim Integrated Products, Inc. that provides data, signaling and power via a single signal serial clock, data input/output (SCIO) pin. This type of one-wire interface or bus requires only two wires: data and ground. The One-Wire® Master may be realized either by a software layer or by means of a hardware module such as a UART to One-wire converter; an I2C to a One-wire converter (e.g. DS2482/DS2483 from Maxim Integrated Products, Inc.); a USB to One-wire converter; or it may be synthesized into an ASIC/FPGA. In addition, control circuitry 215 also includes a CPU 260 such as a microcontroller, a FPGA, a processor, a programmable logic and/or a combination of any of these devices. The output of the control circuitry 215 generated by I/O block 265 is a control signal (SW_ON/OFF) for configuring the settings of each of switches SW1 and SW2. Analog signal supply voltage AVDD supplies the sensor/transducer excitation voltage reference and alternately the power necessary for reading data from/writing data to the memory.

Figure 4:
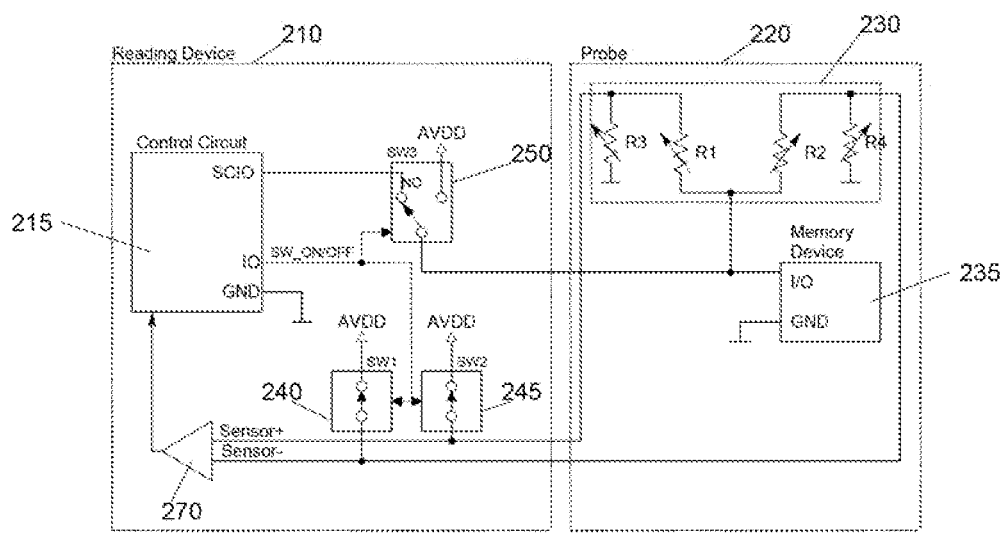
FIG. 4 is a schematic diagram of the system of FIG. 2A wherein the three switches in the reading device are set in a memory access mode in which access is provided for either writing data to/reading data from the memory device embedded in the probe.

In operation, as depicted in FIG. 4, when the reading device seeks access to (i.e., write data to or read data from) the memory device 235, the control signal output (SW_ON/OFF) generated by the control circuit 215 sets the orientation of each of switches SW1 and SW2 to enable a first mode or Memory Access Mode. In this first mode, SW1 240 and SW2 245 are connected to the excitation power supply voltage (AVDD) (e.g., 5V), while switch SW3 250 is configured to connect the control circuit 215 of the reading device 210 to the memory device 235. While in this first mode, configuration or state, the excitation power supply voltage AVDD is not applied to the sensor/transducer 230. Instead, resistors R1 and R2 of the Wheatstone bridge 230 connected via the I/O line of the One-Wire® memory device 235 act as a pull-up resistor pulling up the current to Vs+ (e.g., 5V). Without such pull-up resistance the data could neither be written to nor read from the memory device 235. It is worthwhile noting that an external pull-up resistor separate from or in addition to those in the Wheatstone bridge may not alternatively be employed to provide the necessary pull-up resistance. The reason being that resistors R3 and R4 connected to ground pull-down and thus defeat or cancel out the functionality provided by such separate or additional external pull-up resistance.

Figure 3:
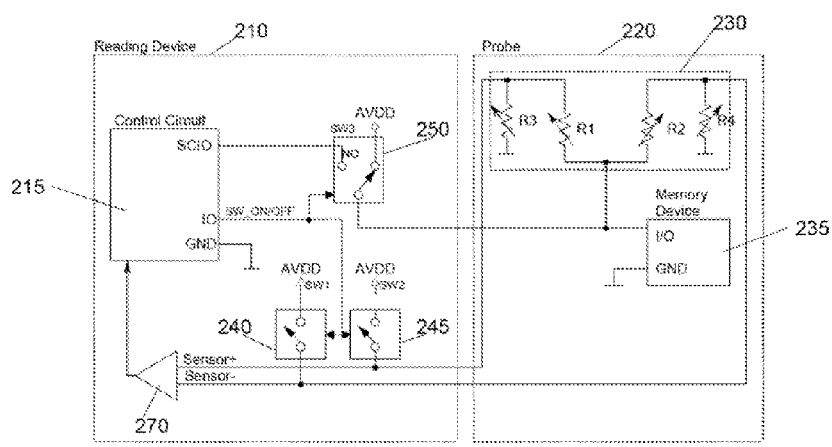
FIG. 3 is a schematic diagram of the system of FIG. 2A wherein the three switches in the reading device are set in a sensor access mode in which access is provided to the sensor/transducer measurements.

A second mode or Sensor Access Mode in which the sensor/transducer output signal of the probe is accessible by reading device 210 is enabled by setting switches SW1 and SW2 so that they are not powered by the excitation power supply voltage AVDD, while switch SW3 connects the excitation power supply voltage AVDD to the memory device 235, as illustrated in FIG. 3. In this second configuration or state, power signal AVDD (e.g., approximately 5 V) is supplied to the Wheatstone bridge 230, while the memory device 235 is placed in standby mode so as not to interfere with the sensor/transducer signals.

Both switches SW1 and SW2 are preferably chosen so that their leakage current does not impact the quality of the measured sensor signals, while the switch SW3 is preferably chosen with a low on resistance (RON) in such a way that it does not impact the quality of the measured sensor signals.

Figure 2B:
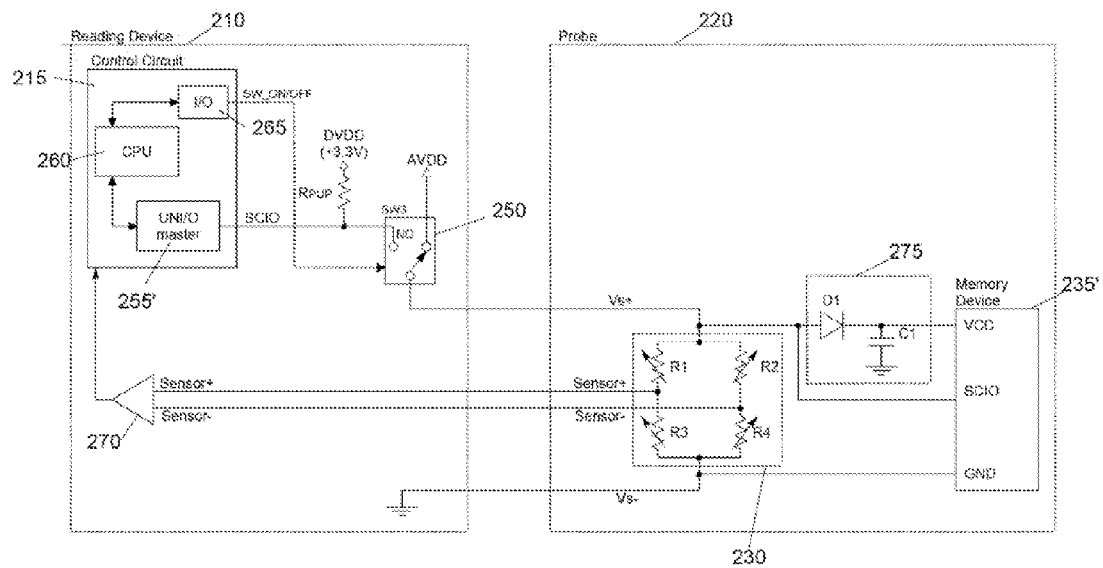
FIG. 2B is an exemplary schematic diagram of another embodiment of a system in accordance with the present invention including a reading device having one switch communicating via a UNI/O protocol using a UNI/O® Master with a probe having a resistive Wheatstone bridge and UNI/O® single I/O memory device embedded therein and one switch.
Figure 2C:
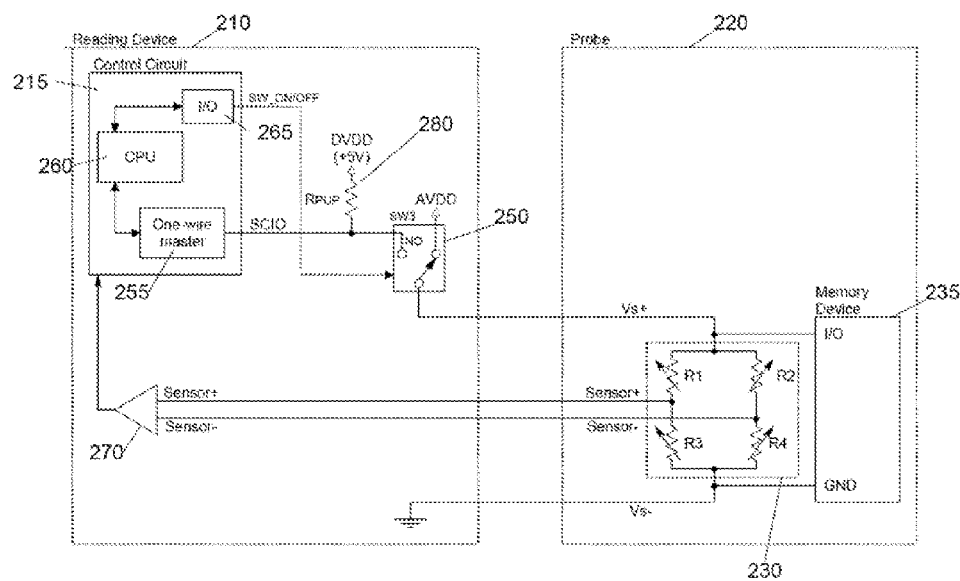
FIG. 2C is an exemplary schematic diagram of yet another system in accordance with the present invention including a reading device having one switch communicating via a one-wire protocol using a One-Wire® Master with a probe having a resistive Wheatstone bridge and a slave One-Wire® memory device embedded therein.

As an alternative, if the impedance of the transducer bridge 230 is relatively high (e.g., approximately 2000 ohms or greater), the bridge may be connected in parallel to the memory device 235 while accessing the memory, during which time the bridge acts as a relatively weak pull down resistor (as shown in FIG. 2C). Power to the memory device is supplied via a digital voltage DVDD (e.g., approximately +5V) This alternative embodiment advantageously eliminates the need for switches SW1 and SW2 wherein switching between the sensor and memory access modes is realized using a single switch SW3 250; however, such configuration is limited to transducer bridges having a relatively high resistance approximately 2000 ohms and greater.

FIG. 2B is an exemplary schematic diagram of an alternative embodiment in accordance with the present invention employing a UNI/O® single I/O EEPROM 235' manufactured by Microchip and a single switch SW3 250. Communication between the reading device and probe is via a UNI/O® Master 255'. Such configuration requires additional circuitry inside the probe. Specifically, a capacitor C1 and a Schottky diode D1 together act as a rectifier 275 to insure that the voltage supply does not fall below the minimal supply voltage level during the data transfer between the reading device 210 and the memory device 235. The capacitor C1 is preferably non-polarized.

Thus, the present inventive circuit configuration advantageously eliminates the need for additional lines/wires/electrical connections between a reading device and a probe when embedding a memory device (e.g., One-Wire® memory device or UNI/O® single I/O memory device in the probe). Although the present claimed invention has been shown and described with respect to only a One-Wire® memory device or UNI/O® memory device embedded in the probe, additional one-wire devices may also be embedded therein. By way of example, a DS 18S20 One-Wire® digital temperature sensor manufactured by Maxim Integrated Products, Inc. may be connected in parallel with the memory device. Furthermore, minimal additional space is required for embedding the memory device in the probe, requiring the addition of only one chip (i.e., the memory device itself). The need for separate or additional pull-up resistance(s) may be eliminated, in accordance with the embodiment in FIG. 2A of the present invention, wherein pull-up resistance necessary for the memory functionality is instead uniquely provided by the Wheatstone bridge. The present inventive configuration realizes the aforementioned advantages by employing circuitry for selecting between two dedicated modes, configurations or states: (i) a first mode or Sensor Access Mode permits access to the sensor(s) measured signal by the reading device, without the memory altering the sensor(s) signal quality; and (ii) a second mode or Memory Access Mode allowing the reading of data from and/or the writing of data to the memory device embedded in the probe.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A monitoring system for a physiological sensor, comprising:
    a reading device; and
    a probe having a housing, wherein the probe is electrically connected to the reading device via a wired interface; wherein the probe comprises:
        a physiological sensor configured as a Wheatstone resistive bridge balancing circuit;
        a memory device integrated within the housing of the probe such that the sensor and memory device are prevented from being separated from one another during use, wherein the memory device is electrically connected in parallel with the sensor;
    wherein communication between the reading device and the probe occurs via the wired interface utilizing a same number of electrical connections between the reading device and the probe as would be required if the memory device were eliminated.

2. The monitoring system in accordance with claim 1, wherein the memory device is a one-wire memory device or a single input/output non-volatile memory device.

3. The monitoring system in accordance with claim 1, wherein the memory device is a non-volatile memory device.

4. The monitoring system in accordance with claim 1, wherein four electrical wires constitute the wired interface between the reading unit and the Wheatstone resistive bridge balancing circuit, not including a shield connection; and two of the four electrical wires constitute the wired interface between the reading unit and the memory device.

5. The monitoring system in accordance with, claim 1, wherein the reading device further comprises electronic control circuitry for reading of data from and/or writing data to the memory device integrated in the probe.

6. The monitoring system in accordance with claim 1, wherein the reading device or the probe further comprises at least one switch for switching between one of two modes: (i) a first mode for reading data from and/or writing data to the memory device; and (ii) a second mode for accessing, data detected by the sensor.

7. The monitoring system in accordance with claim 6, wherein the monitoring system has three switches.

8. The system in accordance with claim 7, wherein the resistive bridge balancing circuit provides all pull-up resistance to access the memory device.

9. The monitoring system in accordance with claim 6, wherein the at least one switch is disposed in the reading device.

10. The monitoring system in accordance with claim 6, wherein the reading device further comprises control circuitry controlling switching status of the at least one switch so as to select between the two modes.

11. The monitoring system in accordance with claim 10, wherein the monitoring system has three switches and the control circuitry controls the switching status of each of the three switches so as to select between the two modes; and wherein two of the three switches are electrically connected between an excitation power supply and the physiological sensor, and a third switch is electrically connected between the control circuitry of the reading device and the memory device of the probe.

12. The monitoring system in accordance with claim 10, wherein the control circuitry of the reading device includes a one-wire interface electrically connected to a processor.

13. The system in accordance with claim 6, wherein the reading device has a single switch to select between the two modes and the reading device further comprises a pull-up resistor electrically connected between the control circuitry of the reading device and an excitation power supply voltage.

14. The system in accordance with claim 1, wherein the probe comprises a device with a one-wire interface connected to the physiological sensor.

15. The system in accordance with claim 14, wherein the probe further comprises a one-wire temperature sensor or a digital I/O port connected in parallel with the memory device.

16. The system in accordance with claim 1, wherein the reading device and the probe share common wire-line connections.

17. A method for operating a monitoring system, wherein the monitoring system includes a reading device and a probe having a housing, and wherein the probe is electrically connected to the reading device via a wired interface, and wherein the probe includes a physiological sensor configured as a Wheatstone resistive bridge balancing circuit and a memory device integrated within the housing of the probe such that the sensor and memory device are prevented from being separated from one another during use, and wherein the memory device is electrically connected in parallel with the sensor, and wherein communication between the reading device and the probe occurs via the wired interface utilizing a same number of electrical connections between the reading device and the probe as would be required if the memory device was eliminated, the method comprising the step of:
    configuring, via a control signal generated by a control circuitry, the switching status of the at least one switch so as to select between the two modes.

18. The method in accordance with claim 17, wherein the monitoring system has three switches and the control signal generated by the control circuitry configures the switching status of each of the three switches to select between the two modes.

19. The method in accordance with claim 17, wherein four electrical wires constitute the wired interface between the reading unit and the probe's Wheatstone resistive bridge, not including a shield connection; and two of the four electrical wires constitute the wired interface between the reading unit and the memory device.

* * * * *